United States Patent [19]

Felix et al.

[11] Patent Number: 4,559,082

[45] Date of Patent: Dec. 17, 1985

[54] HERBICIDE COMPOSITIONS OF EXTENDED SOIL LIFE

[75] Inventors: Raymond A. Felix, Richmond; Joanna K. Hsu, Sunnyvale, both of Calif.

[73] Assignee: Stauffer Chemical Co., Westport, Conn.

[21] Appl. No.: 522,931

[22] Filed: Aug. 12, 1983

[51] Int. Cl.$^4$ .................. A01N 31/00; A01N 37/00; A01N 41/00

[52] U.S. Cl. .......................... 71/98; 71/88; 71/100; 71/103; 71/118; 71/90

[58] Field of Search .................. 71/98, 100, 103

[56] References Cited

U.S. PATENT DOCUMENTS

| | | | |
|---|---|---|---|
| 2,913,327 | 11/1959 | Tilles et al. | 71/100 |
| 3,330,643 | 7/1967 | Harman et al. | 71/88 |
| 3,772,023 | 11/1973 | Nakajima et al. | 430/621 |
| 3,777,024 | 12/1973 | Martin et al. | 514/94 |
| 3,871,865 | 3/1975 | Teach | 71/98 |
| 4,378,239 | 3/1983 | Hyzak et al. | 71/100 |
| 4,381,196 | 4/1983 | Hyzak | 71/100 |
| 4,422,869 | 12/1983 | Hyzak et al. | 71/100 |

FOREIGN PATENT DOCUMENTS

| | | |
|---|---|---|
| 58116403 | 12/1981 | Japan . |
| 58-128305 | 1/1982 | Japan . |
| 28150 | 3/1970 | South Africa . |

OTHER PUBLICATIONS

Parham et al., "Heterocyclic Vinyl Ethers, etc.", (1956) CA51, p. 1965f, (1957).
Sato et al., "Derivatives of Propargyl, etc.", (1956) CA53, p. 5112e (1959).

*Primary Examiner*—Glennon H. Hollrah
*Assistant Examiner*—Andrew Duff Meikle
*Attorney, Agent, or Firm*—Leona L. Lauder; Harry A. Pacini

[57] ABSTRACT

Herbicidally active thiocarbamates are employed in combination with certain unsaturated aryl sulfides, sulfoxides or sulfones having the formula

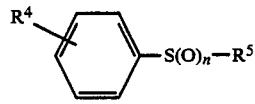

in which $R^4$ is hydrogen, halogen, $C_1$–$C_6$ alkyl or $C_1$–$C_6$ alkoxy; $R^5$ is $C_2$–$C_6$ haloalkenyl or $C_2$–$C_6$ alkynyl; and n equals 0 or 2. In a typical application, the unsaturated aryl sulfide, sulfoxide or sulfone is included in sufficient quantity to lessen the rate of soil degradation of the thiocarbamate. As a result, the herbicidal effectiveness of the thiocarbamate is enhanced and prolonged, rendering a single application of the herbicide effective over a longer period of time.

13 Claims, No Drawings

HERBICIDE COMPOSITIONS OF EXTENDED SOIL LIFE

BACKGROUND OF THE INVENTION

This invention relates to herbicidal compositions, their methods of use, and their preparation. In particular, this invention relates to herbicidal compositions comprising an herbicidally active thiocarbamate in combination with certain unsaturated aryl sulfides, sulfoxides and sulfones, the latter serving to prolong the effectiveness of a single application of the thiocarbamate in controlling undesired plant growth.

Many of the compounds herein disclosed are known compounds, however, one of the compounds herein exemplified, namely, 4-methoxyphenyl-1-propynyl sulfide having the formula

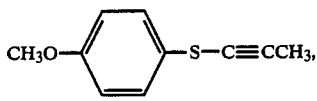

is a novel compound. Most of the references which have disclosed compounds within the generic formula of the instant invention, show their utility to be only as chemical intermediates in various syntheses. Martin et al., U.S. Pat. No. 3,777,024, discloses some aryl propargyl sulfides as insecticidal synergists, and Martin et al., South African Pat. No. 28,150, discloses such compounds as endo- and ectoparasiticides. Neither patent discloses such compounds in combination with thiocarbamate herbicides, or as having any soil extender properties for any herbicides.

Thiocarbamates are well known in the agricultural art as herbicides useful for weed control in crops such as corn, potatoes, beans, beets, spinach, tobacco, tomatoes, alfalfa, rice and others. Thiocarbamates are primarily used in pre-emergence application, and are particularly effective when incorporated into the soil prior to the planting of the crop. The concentration of the thiocarbamate in the soil is greatest immediately after application of the compound. How long thereafter the initial concentration is retained depends in large part on the particular soil used. The rate at which the thiocarbamate concentration declines following its application varies from one type of soil to the next. This is evident both in the observable extent of weed control and in the detectable presence of undegraded thiocarbamate remaining in the soil after considerable time has elapsed.

It is therefore an object of this invention to increase the soil persistence of thiocarbamate herbicides and thus improve their herbicidal effectiveness.

BRIEF DESCRIPTION OF THE INVENTION

It has now been discovered that the soil persistence of certain herbicidally active thiocarbamates is significantly extended by the further addition to the soil of certain extender compounds in the form of certain unsaturated aryl sulfides, sulfoxides and sulfones, which have little or no herbicidal activity of their own and do not decrease the herbicidal activity of the thiocarbamate. This improvement in the soil persistence of thiocarbamates manifests itself in a variety of ways. It can be shown, for example, by soil analyses taken at regular intervals, that the rate of decrease of the thiocarbamate content of the soil is substantially lessened. However, more preferably, improved soil persistence can also be shown by improvements in herbicidal efficacy, as evidenced by a higher degree of weed injury brought about when the extender compound increases the soil persistence of the thiocarbamate, prolonging its effective life.

In particular, this invention relates to novel herbicidal compositions comprising (a) an herbicidally effective amount of a thiocarbamate having the formula

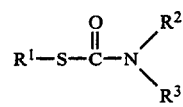

in which $R^1$ is $C_1$–$C_6$ alkyl or $C_3$–$C_6$ alkenyl, optionally substituted with one, two or three halogen atoms; and $R^2$ and $R^3$ are either selected independently from $C_1$–$C_6$ alkyl or combined to conjointly form $C_4$–$C_7$ alkylene; and (b) an amount of an unsaturated aryl sulfide, sulfoxide or sulfone sufficient to extend the soil life of said thiocarbamate, said sulfide, sulfoxide or sulfone having the formula

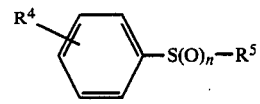

in which $R^4$ is hydrogen, halogen, $C_1$–$C_6$ alkyl or $C_1$–$C_6$ alkoxy;

$R^5$ is $C_3$–$C_6$ haloalkenyl or $C_2$–$C_6$ alkynyl; and n is 0, 1 or 2.

Within the scope of the present invention, the following embodiments are preferred, namely:

in the thiocarbamate formula, $R^1$, $R^2$ and $R^3$ are preferably $C_2$–$C_4$ alkyl, and most preferably $R^1$ is ethyl and $R^2$ and $R^3$ are each propyl; and in the sulfide, sulfoxide or sulfone formula, $R^4$ is preferably hydrogen, halogen, $C_1$–$C_4$ alkyl or $C_1$–$C_4$ alkoxy; $R^5$ is preferably $C_3$–$C_4$ haloalkenyl or $C_3$–$C_4$ alkynyl; and n is 0 or 2. More preferably, $R^4$ is hydrogen, methyl, methoxy or halogen; $R^5$ is propynyl, propargyl or haloallyl; and most preferably $R^4$ is hydrogen, methyl or halogen, $R^5$ is propynyl or propargyl and n is 0.

This invention also relates to a method of controlling undesirable vegetation comprising applying the above composition to the locus where control is desired.

This invention further relates to a novel dehydrohalogenation process for preparing the aryl alkynyl sulfide extender compounds disclosed herein.

The term "alkyl" is used herein in its normal meaning and is intended to include both straight-chain and branched-chain groups.

The term "herbicide", as used herein, means a compound or composition which adversely controls or modifies the growth of plants. By the term "herbicidally effective amount" is meant any amount of such compound or composition which adversely causes a modifying effect upon the growth of plants. By "plants" is meant germinant seeds, emerging seedlings and established vegetation, including roots and above-ground portions. Such adverse controlling or modifying effects include all deviations from natural development, such as killing, retardation, defoliation, desiccation, regulation, stunting, tillering, stimulation, leaf burn, dwarfing and the like.

The phrase "to extend the soil life of said thiocarbamate" as used herein means to retard the rate at which molecules of thiocarbamate are broken down into decomposition products when in contact with soil and/or to prolong the period of time following application in which herbicidal effects can be observed. This applies both to field sites where repeated applications of thiocarbamates have resulted in decreasing herbicidal effectiveness, and to field sites where a decline in activity is detected over time regardless of the prior history of herbicidal applications. An extended soil life can be manifested in a slower rate of decline of weed-killing activity, or an increased half-life of thiocarbamate concentration in the soil. Other techniques of determining soil life are readily apparent to one skilled in the art.

DETAILED DESCRIPTION OF THE INVENTION

According to the present invention, the above-described unsaturated aryl sulfides, sulfoxides or sulfones are applied to prolong the molecular integrity and herbicidal effectiveness of the thiocarbamates. As the examples below indicate, there is no critical range of the ratio of these two components. The soil life-extending effect is observable over a broad range of ratios. It is most convenient, however, to apply the compounds at a ratio of from about 0.2:1 to about 15:1 (thiocarbamate:unsaturated aryl sulfide, sulfoxide or sulfone). Preferably, the ratio ranges from about 0.5:1 to about 8:1, and most preferably from about 0.5:1 to about 6.5:1.

Thiocarbamates which are useful in the present invention inlcude S-ethyl N,N-dipropyl thiocarbamate, S-ethyl N,N-diisobutyl thiocarbamate, S-propyl N,N-dipropyl thiocarbamate, S-propyl N,N-butylethyl thiocarbamate, S-2,3,3-trichloroallyl diisopropyl thiocarbamate, S-2,3-dichloroallyl diisopropyl thiocarbamate and S-ethyl-hexahydro-1H-azepine-1-carbothioate. The thiocarbamates within the scope of the present invention can be prepared by the process described in U.S. Pat. No. 2,913,327 (Tilles et al., Nov. 17, 1959) or U.S. Pat. No. 3,330,643 (Harman et al., July 11, 1967).

The unsaturated aryl sulfides, sulfoxides and sulfones which are useful in the present invention include 4-propargylthio-chlorobenzene (Compound 1); 4-chlorophenyl propargyl (Compound 2); para-chlorophenyl-1-propynyl sulfide (Compound 3); phenyl-1-propynylsulfide (Compound 4); 1-phenylsulfonyl-1-propyne (Compound 5); 2-chloroallyl-4-methylphenyl sulfide (Compound 6); 2-chloroallyl-4-methoxyphenyl sulfide (Compound 7); 4-methylphenyl-1-propynyl sulfide (Compound 8); and 4-methoxyphenyl-1-propynylsulfide (Compound 9).

The extender compounds claimed herein can be prepared by a variety of known techniques, for example, by methods described in the following references: Andersen, W. K. et al., *Synthesis of 2-Methylbenzo[b]furans and 2-Methylbenzo[b]thiophens*, J.C.S. Chem. Comm. 1974 (5), p. 174; Nakajima et al., U.S. Pat. No. 3,772,023; Iddon B. et al., *Adv. Heterocyclic Chem.*, 1970 (11) p. 177; Truce, W. E. et al., *Sterochemistry of Amine Additions to Acetylenic Sulfones*, J. Org. Chem. 1975 (40) p. 3200 (at 3250); Andersen, W. K. et al., *Use of 2,3-Dichloropropene and 1,3-Dichlorobut-2-ene as Synthons for Heterocyclic Compounds. Synthesis of 2-Methylbenzo[b]furans, 2-Methyl-benzo[b]thiophens, and 4-Methyl-2H-chromen*, J. Chem. Soc. 1976 (1) 1; Hill, C. J. et al., *The Mass Spectral Rearrangements of Aryl Propenyl Sulfones. An Electron Impact Induced Smiles Type Rearrangement*, Org. Mass. Spec., 1977 (12) p. 379; and Martin et al., U.S. Pat. No. 3,777,024.

In broad outline, the aryl haloalkenyl sulfides can be prepared by combining dihalo-alkenes with an appropriately substituted thiophenol in the presence of a base such as potassium carbonate, triethylamine, sodium hydroxide or an alkoxide.

The aryl alkynyl sulfides of the instant invention can be prepared by the dehydrohalogenation of appropriate aryl haloalkenyl sulfides. A strong base is required for the reaction, preferably an alkali metal salt of an amine, ammonia, an alkoxide or an hydroxide. The latter is a novel and preferred base. The most preferred base is an aqueous solution of from 40–60% sodium hydroxide, with a more preferred solution range being from 45–55% and the most preferred concentration being 50%. The use of such a base is novel, economical and aids in phase separation.

The dehydrohalogenation reaction is run in a mixed phase system with a phase transfer catalyst, such as benzyl triethyl ammonium chloride, tetrabutyl phosphonium bromide, tetrabutyl ammonium bromide, or Aliquot ® 336 (tricaprylyl methyl ammonium chloride). In general, an inert solvent, such as tetrahydrofuran (THF), ether, benzene, or toluene is employed. Where an hydroxide salt is used in the reaction, the solvent can be methylene chloride or 1,1,2-trichlorethane.

The preferred temperature for such a process is between $-30°$ C. and $150°$ C. A more preferred temperature range for such a reaction is from $0°$ C. to $110°$ C., and the most preferred temperature range is from $20°$ C. to $45°$ C.

Such a reaction is illustrated by the example below of the preparation of the novel compound 4-methoxyphenyl-1-propynyl sulfide.

Preparation of 4-Methoxyphenyl-1-propynyl sulfide

Seven and two-tenths grams (7.2 g; 0.034 mole) of para-methoxyphenyl 2-chloroallyl sulfide was combined with 10 milliliters (ml) of 50% NaOH solution (0.087 mole), 0.5 g of the phase transfer catalyst tetrabutyl phosphonium bromide, and 5 ml of the inert solvent methylene chloride. The mixture was stirred and then allowed to stand at room temperature over the weekend. Standard work-up procedures were employed.

The yield was 4.8 g. The expected product was confirmed by NMR (nuclear magnetic resonance), IR (infrared refraction) and MS (mass spectroscopy).

Preparation of 4-Methylphenyl-1-propynyl sulfide

Six and nine-tenths grams (6.9 g) of para-methylphenyl 2-chloroallyl sulfide was combined with 10 ml of 50% NaOH solution, 0.5 g of the phase transfer catalyst tetrabutyl phosphonium bromide, and 5 ml of the inert solvent methylene chloride. The mixture was stirred and then allowed to stand at room temperature over the weekend. Standard work-up procedures were employed.

The yield was 4.8 g. The expected product was confirmed by both NMR, IR and MS.

Different types of aryl alkynyl sulfides can be prepared by rearrangement of the triple bond. (See for example, Pourcelot, G. et al., *Cinetique et Mecanisme da la Reaction de Prototropic des Composes Propargyliques*,

*Alleniques et Propynyliques Portant un Heteroatome (Colonne Vb et VIb)*, Tetrahedron 1982 (38) p. 2123.)

The aryl unsaturated sulfoxides and sulfones claimed herein can be prepared from the corresponding sulfides by oxidation with one or two equivalents of meta-chloro perbenzoic acid, respectively.

The objects of the present invention are achieved by applying the unsaturated aryl sulfide and sulfone extender compounds to the soil at an agricultural field site in conjunction with the thiocarbamate herbicide. The extender and herbicide can be applied simultaneously in a single mixture or in separate formulations, or they can be applied in succession, with either one following the other. In successive application, it is preferable to add the compounds as close in time as possible.

The variety of crops on which the present composition is useful can be significantly broadened by the use of an antidote to protect the crop from injury and render the composition more selective against weeds.

For antidote descriptions and methods of use, reference is made to U.S. Pat. No. 3,959,304 issued to E. G. Teach on May 25, 1976; U.S. Pat. No. 3,989,503 issued to F. M. Pallos et al. on Nov. 2, 1976; U.S. Pat. No. 4,021,224 issued to F. M. Pallos et al. on May 3, 1977; U.S. Pat. No. 3,131,509 issued to O. L. Hoffman on May 5, 1964; and U.S. Pat. No. 3,564,768 issued to O. L. Hoffman on Feb. 3, 1971.

Useful antidotes include acetamides having the formula

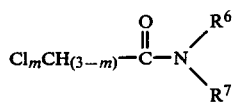

in which m is 1 or 2, and $R^6$ and $R^7$ are independently $C_1$–$C_{12}$ alkyl or $C_2$–$C_{12}$ alkenyl. Examples falling within the above formula are N,N-diallyl dichloroacetamide and N,N-diallyl chloroacetamide.

Further useful antidotes are oxazolidines and thiazolidines having the formula

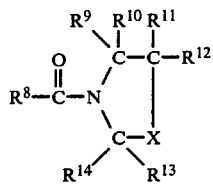

in which $R^9$ is $C_1$–$C_4$ alkyl, haloalkyl, or dihaloalkyl, $R^9$ through $R^{14}$ are independently hydrogen or methyl, and X is oxygen or sulfur. An example of such an antidote is 2,2,5-trimethyl-N-dichloroacetyl oxazolidine ($R^8$=CHCl$_2$, $R^9$=$R^{10}$=$R^{11}$=H, $R^{12}$=$R^{13}$=$R^{14}$=CH$_3$, X=O).

Other useful antidotes include 1,8-naphthalic anhydride and 2,2-spiro-cyclohexane-N-dichloroacetyl oxazolidine.

For maximum effect, the antidote is present in a non-phytotoxic, antidotally effective amount. By "non-phytotoxic" is meant an amount which causes at most minor injury to the crop. By "antidotally effective" is meant an amount which substantially decreases the extent of injury caused by the herbicide to the crop. The preferred weight ratio of herbicide to the crop is about 0.1:1 to about 30:1. The most preferred range for this ratio is about 3:1 to about 20:1.

The extender compounds for which test results are recorded below are as follows:

TABLE I

| Extender Compound No. | Structure | Name |
|---|---|---|
| 1 | Cl—⟨⟩—S—CH$_2$—C≡CH | 4-propargylthio-chlorobenzene |
| 2 | Cl—⟨⟩—S(=O)$_2$—CH$_2$—C≡CH | 4-chlorophenyl propargyl sulfone |
| 3 | Cl—⟨⟩—S—C≡CCH$_3$ | p-chlorophenyl 1-propynyl sulfide |
| 4 | ⟨⟩—S—C≡CCH$_3$ | phenyl-1-propynyl sulfide |
| 5 | ⟨⟩—S(=O)$_2$—C≡CCH$_3$ | 1-phenyl sulfonyl-1-propyne |
| 6 | CH$_3$—⟨⟩—S—CH$_2$C(Cl)=CH$_2$ | 2-chloroallyl-4-methylphenyl sulfide |
| 7 | CH$_3$O—⟨⟩—S—CH$_2$C(Cl)=CH$_2$ | 2-chloroallyl-4-methoxyphenyl sulfide |
| 8 | CH$_3$—⟨⟩—S—C≡CCH$_3$ | 4-methylphenyl-1-propynyl sulfide |
| 9 | CH$_3$O—⟨⟩—S—C≡CCH$_3$ | 4-methoxyphenyl-1-propynyl sulfide |

The following examples are offered to illustrate the utility of the present invention, and are intended neither to limit nor define the invention in any manner.

EXAMPLE 1

Herbicidal Activity Improvement Tests

This example offers herbicidal activity test data for the abovereferenced compounds to show the effectiveness of the range of extender compounds of the instant invention in improving the herbicidal activity of thiocarbamates. The effect is observed by comparing the extent of weed control in test flats treated with a thiocarbamate against that occurring in similar flats treated with both the thiocarbamate and the extender. The soil used in these tests was a sandy loam soil from Sunol, Calif., which was pre-treated with the herbicide to simulate a typical field which had received previous herbicide applications.

A. Soil Pre-Treatment

A solution was prepared by diluting an emulsifiable liquid concentrate containing 6 lb/gal (0.72 kg/l) (76.8% by weight) of the herbicide S-ethyl di-n-propylthiocarbamate in 200 ml of water, such that the resulting concentration of herbicide in the solution was 2000 mg/l. Two hundred ml of this solution was then added to 200 lb (90.8 kg) of soil to which 17-17-17 fertilizer (N-P$_2$O$_5$-K$_2$0 on a weight basis) had been previously added to a concentration of 50 ppm by weight with respect to the soil. The mixture was mixed in a rotary mixer for 10 to 30 minutes.

The soil was then placed in round plastic containers, 7.5 inches (19.0 cm) in diameter by 7.5 inches (19.0 cm) deep. The soil was tamped and leveled with a row marker to impress three rows across the width of each container. One row was seeded with DeKalb XL-45A corn (*Zea mays*), and two rows were seeded with barnyardgrass (*Echinochloa crusqualli*). Sufficient seeds were planted to produce several seedlings per row. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen to remove plant roots and clods.

B. Herbicide Test

The same thiocarbamate preparation described in Part A was used. The extender compounds were used in technical form. These materials were added to 100 cc mixtures of equal parts of water and acetone at such amounts that 5 cc of the resulting mixture when added to three pounds of soil yielded a quantity in the soil equivalent to the desired application rate expressed in pounds per acre. Thus 5 cc of the mixture and three pounds of soil were placed in a rotary mixer.

The treated soil was then placed in aluminum flats which were approximately 3 inches deep, 4 inches wide, and 8 inches long (7.6×10.2×20.3 cm). The soil was tamped and leveled with a row marker to impress six rows across the width of the flat. The test weeds were as follows:

| COMMON NAME | ABBREVIATION | SCIENTIFIC NAME |
|---|---|---|
| watergrass | WG | *Echinochloa crusgalli* (L.) |
| wild oats | WO | *Avena fatua* (L.) |
| wild cane | WC | *Sorghum bicolor* (L.) Moench |
| yellow foxtail | YF | *Setaria lutescens* (Weigle) Hubb. |
| annual ryegrass | AR | *Lolium temulentum* |

Rox orange and R-10 milo (both *Sorghum bicolor*) were also used in some of the experiments as a plant growth indicators.

DeKalb XL-45A or XL-25A corn of species *Zea mays* (L.) was also planted.

Sufficient seeds were planted to produce several seedlings per inch in each row. The flats were then placed in a greenhouse maintained at 70° to 85° F. (21° to 30° C.) and watered daily by sprinkler.

Approximately three weeks after treatment, the degree of weed control and corn injury were estimated and recorded as a percentage compared to the growth of the same species in a check flat of the same age which had been seeded in conditioned soil but not treated with either an herbicide or an extender. The rating scale ranges from 0 to 100%, where 0 equals no effect with plant growth equal to the untreated check, and 100 equals complete kill.

The results are listed in Table I. Each alphabetized test represents a separate batch of experiments. Control experiments (herbicide alone with no extender present) were included in each batch for comparison. Substantial improvements in average percent weed control over the control experiments are evident. The herbicidal efficacy of the thiocarbamate three weeks after application was much improved by the use of the extender, whereas the corn remained unaffected.

TABLE II

HERBICIDE TEST RESULTS
HERBICIDE: S—Ethyl, N,N—dipropylthiocarbamate (EPTC) at 3 lb/A
EXTENDER: Indicated by Compound Numbers in Table I; application rates are shown in Table.

| Test No. | Extender Cmpd. No. | Rate (lb/A) | Water-grass | R-10 Milo | Wild Oats | Wild cane | Annual rye | Yellow foxtail | Rox orange | Corn | Ave. % Control |
|---|---|---|---|---|---|---|---|---|---|---|---|
| A | Control* | — | 0 | 0 | 0 | 0 | 0 | NT | NT | 0 | 0 |
| A | 4 | 2 | 50 | 80 | 50 | 40 | 100 | NT | NT | 0 | 64 |
| A | 4 | 4 | 85 | 95 | 80 | 80 | 100 | NT | NT | 0 | 88 |
| B | Control* | — | 0 | 0 | 0 | 0 | NT | 0 | NT | 0 | 0 |
| B | 2 | 4 | 15 | 60 | 30 | 0 | NT | 0 | NT | 0 | 21 |
| B | 3 | 4 | 65 | 80 | 70 | 70 | NT | 10 | NT | 0 | 59 |
| C | Control* | — | 0 | 0 | 0 | NT | 0 | NT | 0 | 0 | 0 |
| C | 1 | 2 | 20 | 85 | 10 | NT | 85 | NT | 85 | 0 | 57 |
| C | 1 | 4 | 65 | 85 | 75 | NT | 95 | NT | 90 | 0 | 82 |
| D | Control* | — | 23 | 35 | 38 | 0 | NT | 0 | NT | 0 | 19 |
| D | 6 | 4 | 65 | 70 | 90 | 45 | NT | 40 | NT | 0 | 62 |
| D | 7 | 4 | 30 | 65 | 75 | 10 | NT | 10 | NT | 0 | 38 |
| D | 8 | 4 | 70 | 85 | 75 | 85 | NT | 40 | NT | 0 | 71 |
| D | 9 | 4 | 80 | 70 | 80 | 25 | NT | 20 | NT | 0 | 55 |
| E | Control* | — | 20 | 15 | 70 | 15 | NT | 10 | NT | 0 | 26 |
| E | 6 | 1 | 20 | 20 | 80 | 40 | NT | 10 | NT | 0 | 34 |
| E | 6 | 2 | 30 | 40 | 90 | 60 | NT | 10 | NT | 0 | 46 |
| E | 6 | 3 | 50 | 40 | 85 | 85 | NT | 40 | NT | 0 | 60 |
| F | Control** | — | 0*** | 23 | 26 | 0 | NT | NT | NT | 0 | 12 |
| F | 5 | 2 | 35*** | 40 | 50 | 30 | NT | NT | NT | 0 | 39 |
| F | 5 | 4 | 68*** | 70 | 70 | 40 | NT | NT | NT | 0 | 62 |

NT = Not Tested
*Control Data - average of two replications.
**Control Data - average of three replications.
***Average of two rows of watergrass.

EXAMPLE 2

Chemical Assay Data

These examples show, by soil analysis, the effectiveness of the compounds of the present invention in extending the soil life of the thiocarbamate herbicides. The herbicide used in these tests was the same as in Example 1, S-ethyl N,N-dipropyl thiocarbamate (EPTC). The soil was a silty loam soil obtained from Mississippi, containing approximately (on a weight basis) 65.2% sand, 31.8% silt, and 3.0% clay, determined by mechanical means. The total organic content of the soil was approximately 0.1% by weight and the pH was 8.1, both determined by chemical analysis.

A. Soil Pre-Treatment

The soil was pre-treated according to the procedure outlined in Part A of Example 1, except that the soil at the end of the procedure is passed through a two millimeter (mm) screen.

B. Soil Persistence Test

A 100-gram quantity (air-dry basis) of the pre-treated soil was placed in an 8 ounce (0.25 liter) wide-mouth glass bottle. The same emulsifiable concentrate described in Part A above was appropriately diluted in water such that a 5-ml portion added to the soil would produce a herbicide concentration of 6 ppm (weight) in the soil. This is equivalent to an application rate of 6 pounds per acre (6.7 kilograms per hectare) in a field where the herbicide is incorporated into the soil through a depth of about 2 inches (5.08 cm) soon after application. A selected extender compound in tehcnical (nonformulated) form was then diluted in an acetonewater mixture such that a one-ml portion added to the soil would produce a concentration of 4 ppm by weight, equivalent to 4 pounds per acre (4.5 kilograms per hectare). On these bases, the herbicide and extender were added to the bottle containing the soil.

Following such treatment, the soil was moistened with 20 ml deionized water. The bottle was then covered with a watch glass to maintain aerobic conditions and to prevent rapid soil drying, and placed in a controlled environmental chamber in darkness, where the temperature was maintained constant at 25° C.

Four days later, the bottle was removed from the environmental chamber and 25 ml of water and 100 ml of toluene were added. The bottle was then tightly sealed with a lid containing a four-layer cellophane liner, and vigorously shaken on a variable speed, reciprocating shaker (Eberback Corp. Model 6000) set at approximately 150 excursions per minute for 90 minutes. After shaking, the bottle contents were allowed to settle, and a 10 ml aliquot of toluene was transferred to pipette into a glass vial and sealed with a polyseal cap. The toluene extract was analyzed for herbicidal content by gas chromatography. The chromatogram data was then converted to equivalent soil concentrations in parts per million (ppm) by weight of the herbicide.

The results are shown in the table below, where a variety of compounds were tested in two separately treated batchs of soil. A control run with the herbicide alone and without an extender was conducted for each soil batch, to show how the drop in herbicide concentration was affected by the extender compound. In each case, the quantity of herbicide remaining in the soil after four days was dramatically increased when the extender compound was added. Many of the tests for which the results are collated below in Table I were run at different times. However, the control without extender and the parallel test with the extender were always run at the same time, and it is the relative differences between the EPTC residues with and without the extender that indicate the extender's effectiveness in prolonging the soil life of the thiocarbamate.

TABLE I

4-DAY SOIL PERSISTENCE DATA
Herbicide: S—Ethyl N,N—di-propylthiocarbamate (EPTC) at 6 lb/A (6 ppm in soil)
Extender: As shown at 4 lb/A (4 ppm in soil)

| Extender Compound No. | EPTC Residue After 4 days (ppm) | |
|---|---|---|
| | With Extender | Without Extender |
| 1 | 0.83 | 0.25 |
| 2 | 2.18 | 0.03 |
| 3 | 3.53 | 0.03 |
| 4 | 2.34 | 0.00 |
| 5 | 3.62 | 0.03 |
| 6 | 2.10 | 0.05 |
| 6 | 2.54 | 0.05 |
| 7 | 0.86 | 0.03 |
| 7 | 1.09 | 0.00 |
| 8 | 3.10 | 0.05 |
| 9 | 2.16 | 0.03 |
| 9 | 2.91 | 0.00 |

METHODS OF APPLICATION

The herbicidal compositions of the present invention are useful in controlling the growth of undesirable vegetation by preemergence or post-emergence application to the locus where control is desired, including pre-plant and post-plant soil incorporation as well as surface application. The compositions are generally embodied in formulations suitable for convenient application, containing additional ingredients, diluents or carriers to aid in their dispersal. Examples of such ingredients or carriers are water, organic solvents, dusts, granules, surface active agents, water-oil emulsions, wetting agents, dispersing agents, and emulsifying agents. The formulated compositions generally take the form of dusts, emulsifiable concentrates, granules, or microcapsules.

A. DUSTS

Dusts are dense powder compositions which combine the active compounds with a dense, free-flowing soild carrier. They are intended for application in dry form and are designed to settle rapidly to avoid being windborne to areas where their presence is not desired.

The carrier may be of mineral or vegetable origin, and is preferably an organic or inorganic powder of high bulk density, low surface area, and low liquid absorptivity. Suitable carriers include micaceous talcs, pyrophyllite, dense kaolin clays, tobacco dust, and ground calcium phosphate rock.

The performance of a dust is sometimes aided by the inclusion of a liquid or solid wetting agent, of ionic, anionic, or nonionic character. Preferred wetting agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Dispersants are also useful in the some dust compositions. Typical dispersants include methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N-(long chain acid) taurates.

In addition, inert absorptive grinding aids are frequently included in dust compositions to aid in the manufacturing of the dust. Suitable grinding aids include attapulgite clay, diatomaceous silica, synthetic fine silica and synthetic calcium and magnesium silicates.

In typical dust compositions, carriers are usually present in concentrations of from about 30 to 90 weight percent of the total composition. The grinding aid usually constitutes about 5 to 50 weight percent, and the wetting agent up to about 1.0 weight percent. Dispersants, when present, constitute up to about 0.5 weight percent, and minor amounts of anticaking and antistatic agents may also be present. The particle size of the entire composition is usually about 30 to 50 microns.

B. EMULSIFIABLE CONCENTRATES

Emulsifiable concentrates are solutions in which the active materials and an emulsifying agent are dissolved in a nonwatermiscible solvent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

C. GRANULES

Granules are physically stable, particulate compositions in which the active ingredients adhere to or are distributed throughout a basic matrix of a coherent, inert carrier with macroscopic dimensions. A typical particle is about 1 to 2 millimeters in diameter. Surfactants are often present to aid in the leaching of the active ingredient from the granule to the surrounding medium.

The carrier is preferably of mineral origin, and generally falls within one of two types. The first are porous, absorptive, preformed granules, such as attapulgite or heat expanded vermiculite. A solution of the active agent is sprayed on the granule at concentrations of up to 25 weight percent of the total weight. The second are powdered materials to which the active ingredients are added prior to being formed into granules. These materials include kaolin clays, hydrated attapulgite, or bentonite clays in the form of sodium, calcium, or magnesium bentonites. Water-soluble salts may also be present to help the granules disintegrate in water. These ingredients are blended with the active components, then granulated or pelleted, followed by drying. In the resulting composition, the active component is distributed uniformly throughout the mass. Granules can be made with as much as 25 to 30 weight percent active component, but more frequently a concentration of about 10 weight percent is desired for optimum distribution. Granule compositions are most useful in a size range of 15–30 mesh.

The surfactant is generally a common wetting agent of anionic or nonionic character. The most suitable wetting agents depend upon the type of granule used. When preformed granules are sprayed with active material in liquid form, the most suitable wetting agents are nonionic, liquid wetters miscible with the solvent. These are compounds generally known as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents usually comprise up to about 5 weight percent of the total composition.

When the active ingredient is first mixed with a powdered carrier and subsequently granulated, liquid nonionic wetters can still be used, but it is usually preferable to incorporate at the mixing stage a solid, powdered anionic wetting agent comprising up to about 2.0 weight percent of the total composition.

Typical granules comprise about 5 to 30 percent by weight active material, about 0 to 5 weight percent wetting agent, and about 65 to 95 weight percent carrier.

D. MICROCAPSULES

Microcapsules are fully enclosed droplets or granules in which the active materials are enclosed in an inert porous membrane which allows the enclosed materials to escape to the surrounding medium at controlled rates.

Encapsulated droplets are typically about 1 to 50 microns in diameter. The enclosed liquid typically constitutes about 50 to 95% of the weight of the capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. IN GENERAL

Each of the above formulations can be prepared as a package containing both the herbicide and the extender together with the other ingredients of the formulation (diluents, emulsifiers, surfactants, etc.), or as a tank mix in which the components are formulated separately and combined at the grower site. The two formulations in the tank mix can be of either the same type or two different types—e.g., the herbicide in microcapsule form and the extender as an emulsifiable concentrate.

As a further alternative, the herbicide and extender can be applied sequentially. This is less preferred, however, since simultaneous application generally produces better results.

In general, any conventional method of application can be used. The locus of application can be soil, seeds, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts and sprays becuase they are effective in very low dosages. In order to modify or control the growth of germinating seeds or emerging seedlings, as a typical example, the dust and liquid compositions are applied to the soil according to conventional methods and are distributed to a depth of at least one-half inch below the soil surface. The compositions can either be mixed with the soil particles by discing, dragging, or mixing operations, or sprayed or sprinkled over the surface of the soil. The compositions can also be added to irrigation water so that they will accompany the water as it penetrates the soil.

The amount of active ingredient required for herbicidal effectiveness depends upon the nature of the seeds or plants to be controlled and the prevailing conditions. Usually, herbicidal effects are obtained with an application rate of about 0.01 to about 50 pounds per acre, preferably about 0.1 to about 25. It will be readily apparent to one skilled in the art that compositions exhibiting lower herbicidal activity will require a higher dosage than more active compounds for the same degree of control.

What is claimed is:

1. An herbicidal composition of extended soil life comprising
   (a) an herbicidally effective amount of a thiolcarbamate having the formula

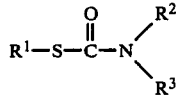

in which
   $R^1$, $R^2$ and $R^3$ are each independently $C_2$-$C_4$ alkyl; and
   (b) an amount of an unsaturated aryl sulfide or sulfone having the formula

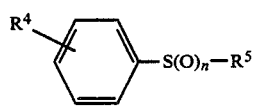

in which
   $R^4$ is hydrogen, halogen, $C_1$-$C_4$ alkyl or $C_1$-$C_4$ alkoxy;
   $R^5$ is $C_2$-$C_6$ haloalkenyl or $C_2$-$C_6$ alkynyl; and
   $n = 0$ or 2;
   sufficient to extend the soil life of said thiolcarbamate.

2. An herbicidal composition as defined in claim 1 wherein n is 0.

3. An herbicidal composition as defined in claim 1 wherein n is 2.

4. An herbicidal composition as defined in claim 1 wherein $R^5$ is $C_3$-$C_4$ alkynyl.

5. An herbicidal composition as defined in claim 1 wherein $R^5$ is $C_3$-$C_4$ haloalkenyl.

6. An herbicidal composition as defined in claim 1 wherein $R^4$ is hydrogen, halogen, $C_1$-$C_4$ alkyl or $C_1$-$C_4$ alkoxy.

7. An herbicidal composition as defined in claim 1 wherein $R^4$ is hydrogen, halogen or methyl and $R^5$ is propynyl or propargyl.

8. An herbicidal composition as defined in claim 1 wherein said thioicarbamate is S-ethyl-N,N-dipropyl thicarbamate.

9. An herbicidal composition as defined in claim 1 wherein said unsaturated aryl sulfide is phenyl-1-propynyl sulfide; 4-propargylthio-chlorobenzene; or 4-methylphenyl-1-propynyl sulfide.

10. An herbicidal composition as defined in claim 1 wherein the weight ratio of said thiolcarbamate to said unsaturated aryl sulfide, sulfoxide or sulfone ranges from about 0.2:1 to about 15:1.

11. An herbicidal composition as defined in claim 1 wherein said weight ratio ranges from about 0.5:1 to about 8:1.

12. A method of controlling undesirable vegetation comprising applying to the locus where control is desired both
    (a) an herbicidally effective amount of a thiolcarbamate having the formula

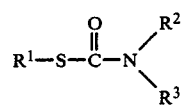

in which
    $R^1$, $R^2$ and $R^3$ are each independently $C_2$-$C_4$ alkyl; and
    (b) an amount of an unsaturated aryl sulfide or sulfone having the formula

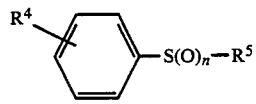

in which
    $R^4$ is hydrogen, halogen, $C_1$-$C_4$ alkyl or $C_1$-$C_4$ alkoxy;
    $R^5$ is $C_2$-$C_6$ haloalkenyl or $C_2$-$C_6$ alkynyl; and
    $n = 0$ or 2;
    sufficient to extend the soil life of said thiolcarbamate.

13. A method of extending the soil life of a thiolcarbamate having the formula

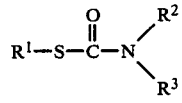

in which
    $R^1$, $R^2$ and $R^3$ are each independently $C_2$-$C_4$ alkyl;
    and comprising applying to the soil containing said thiolcarbamate or to which said thiolcarbamate is to be applied an effective amount of an unsaturated aryl sulfide or sulfone having the formula

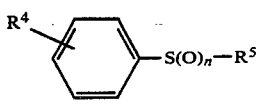
in which
R⁴ is hydrogen, halogen, $C_1$–$C_4$ alkyl or $C_1$–$C_4$ alkoxy;
$R^5$ is $C_2$–$C_6$ haloalkenyl or $C_2$–$C_6$ alkynyl; and
n=0 or 2;
sufficient to extend the soil life of said thiolcarbamate.
* * * * *